United States Patent [19]

Chauvin et al.

[11] Patent Number: 4,642,408

[45] Date of Patent: Feb. 10, 1987

[54] METHOD FOR THE REMOVAL OF NICKEL, ALUMINUM AND CHLORINE FROM OLEFIN OLIGOMERS

[75] Inventors: Yves Chauvin, Le Pecq; Dominique Commereuc, Meudon, both of France

[73] Assignee: Institut Francais du Petrole, Rueil-Malmaison, France

[21] Appl. No.: 725,728

[22] Filed: Apr. 22, 1985

[30] Foreign Application Priority Data

Apr. 20, 1984 [FR] France ................................ 84 06280

[51] Int. Cl.$^4$ ............................ C07C 7/00; C07C 7/10
[52] U.S. Cl. .................................... 585/836; 585/861; 585/868; 585/853
[58] Field of Search ............... 585/836, 861, 868, 853, 585/531, 532

[56] References Cited

U.S. PATENT DOCUMENTS 3,655,794  4/1972  Strache et al. ...................... 585/861
3,703,559  11/1972  Kerfoot et al. ...................... 585/868
4,028,485  6/1977  Poloso et al. ........................ 585/836

Primary Examiner—Andrew H. Metz
Assistant Examiner—Chung K. Pak
Attorney, Agent, or Firm—Millen & White

[57] ABSTRACT

Nickel, aluminum and chlorine derivatives which remain dissolved in olefin oligomers after oligomerization in the presence of a catalyst comprising nickel, aluminum and chlorine compounds, are removed from the crude product by treatment with:
  oxygen or a gas containing oxygen,
  anhydrous ammonia, and
  a solution of an alkali metal hydroxide.

10 Claims, No Drawings

METHOD FOR THE REMOVAL OF NICKEL, ALUMINUM AND CHLORINE FROM OLEFIN OLIGOMERS

This invention relates to a method for the removal of nickel, aluminum and chlorine compounds dissolved in the crude product derived from the oligomerization of mono-olefins.

Methods for the dimerization and/or codimerization of mono-olefins, for example, those having 2 to 4 carbon atoms, such as ethylene, propylene, 1- and 2-butenes, in the presence of a catalyst comprising a mixture of a nickel salt or complex soluble in hydrocarbons and an aluminum organo-chloride are disclosed in U.S. Pat. No. 3,655,810, European Patent No. 12.685 and French patent No. 2.464.243.

However, in the application of the method on an industrial scale there arises the difficulty of eliminating inorganic parts of the catalyst remaining in the resultant olefin oligomerizate, which is unacceptable for many of the uses of the oligomerizate.

Simply washing the oligomerizate has proved to be ineffective for the removal of impurities as this leads to the formation of a gelatinous alumina precipitate and causes the formation of chlorinated hydrocarbon derivatives and of a hydrophobic mixture of nickel hydroxide and colloidal metallic nickel which cannot easily be removed from the solution. In addition, a large proportion of nickel remains in the hydrocarbon phase in the form of a soluble, stable complex which, however, decomposes in the reboiler during subsequent distillation.

The utilization of an aqueous solution of an alkali metal hydroxide avoids the formation of a gelatinous alumina precipitate, but does not prevent the formation of chlorinated hydrocarbons.

Treatment of the oligomerizate with anhydrous ammonia, followed by washing with an aqueous solution of an alkali metal hdyroxide, such as is described in French Patent No. 2 114 114 prevents the formation of a gelatinous alumina precipitate and that of chlorinated hydrocarbons, but does not prevent that of a hydrophobic suspension of nickel derivatives which remains at the aqueous interface during phase separation and does not remove the nickel compounds soluble in the hydrocarbon phase.

None of these mthods results in a satisfactory purification of the oligomerizate. The object of this invention consists in providing a method for the purification of an olefin oligomerizate and in particular the removal of nickel compounds which remain in the oligomerizate after reaction.

According to the invention, the crude liquid product resulting directly from the oligomerization of a lower olefin in the presence of the chlorinated catalyst mentioned above is (1) first treated with anhydrous ammonia, and (2) subsequently washing with an aqueous solution of an alkali metal hydroxide. The crude liquid product is treated with oxygen or a gas containing oxygen before or after the above methods (1) and (2) or simultaneously with these methods. Operating in this manner overcomes the above-mentioned difficulties and in particular, there remains practically no soluble nickel derivatives in the hydrocarbon phase and no hydrophobic colloidal nickel metal particles are formed. By this treatment the nickel is converted into an insoluble compound which is easily separated from the products, and which appears to consist of a double nickel aluminum hydroxide.

During the above treatment, oxygen is advantageously used in a quantity such that the oxygen/nickel mole ratio is about 0.1:1 to 10:1 and preferentially 0.2:1 to 2:1. The oxygen can be introduced as such but it is preferable to use a mixture of oxygen with an inert gas such as, for example, nitrogen or a mixture of air and nitrogen or air itself. The oxygen content of the mixture can be between 2 and 30% by volume. The contact time of the oxygen-containing gas with the oligomerizate is, for example, between about 0.1 second and 10 minutes, preferably between 0.1 second and 10 seconds and more precisely between 0.1 second and 5 seconds.

In the above treatment, anhydrous ammonia is added in liquid or gaseous form in quantities such that the molar ratio of ammonia to chlorine present in any form in the hydrocarbon phase is between 1:1 and 10:1 and preferably between 1:1 and 3:1, and more precisely, between 1.5:1 and 2:1. The contact time of ammonia with the hydrocarbon mixture is of the order of 0.1 second to 10 minutes, preferably 0.1 to 10 seconds and more precisely 0.1 second to 5 seconds.

The organic phase resulting from the preceding treatment with anhydrous ammonia is then washed with an aqueous solution of an alkali metal hydroxide containing preferably 10 to 25% by weight of said hydroxide. The ratio by volume of the organic phase to the aqueous phase is about 100:1 to 1:1 and preferably 40:1 to 1:1.

When the raw liquid material is first treated with oxygen or a gas containing oxygen and then with anhydrous ammonia and finally washed with an aqueous solution of alkali metal hydroxide, there remains about 1 to 4 ppm by weight of nickel in the organic phase, regardless of what the contact time might have been.

According to a particular embodiment, a first treatment with oxygen precedes the treatment with ammonia and a second treatment with oxygen is applied during or after treatment with the solution of alkali metal hydroxide. The nickel content is then, for example, less than 1 ppm by weight.

The above two treatments with oxygen are preferably carried out under the same conditions, that is, addition of a gas containing oxygen in a quantity such that the oxygen/nickel molar ratio is about 0.1:1 to 10:1.

In the above treatment in the case where oxygen or the oxygen-containing gas is not introduced before treatment with anhydrous ammonia, but before or simultaneously with the treatment with the aqueous solution of alkali metal hydroxide, the nickel remaining dissolved in the organic phase has been found to be less than 1 ppm by weight.

When the above treatment is effected without oxygen or without a gas containing oxygen, the amount of nickel remaining dissolved in the organic phase is 5 to 10 ppm by weight.

It is often advantageous to bring into contact simultaneously the hydrocarbon phase with the aqueous solution of an alkali metal hydroxide and the gas containing oxygen. The contact time is for example in the range of 0.1 second to 10 minutes, preferably 0.1 to 10 seconds and more precisely 0.1 to 5 seconds.

The treatments are carried out at a temperature between 0° C. and 100° C. but it is often preferable, for practical reasons, to carry out these treatments at a temperature close to that of the oligomerization reaction, that is, 20° C. to 80° C. The most preferred temperature is between 30° C. and 60° C.

The pressure must be sufficient to maintain the reaction mixture in a substantially liquid form. A pressure between 0.1 MPa and 5 MPa is generally satisfactory.

On completion of the treatments, the mixture of products separates into several phases: a gaseous phase consisting mainly of inert gas (nitrogen, for example) and which if necessary escapes reducing the pressure; a basic aqueous phase; an organic phase. The aqueous phase is separated from the organic phase and can be re-used for another operation. The organic phase is then washed with water, and then subjected to fractional distillation to separate the products. The insoluble, double aluminum-nickel hydroxide is separated from the aqueous phase by any known method, such as filtration or settling.

The method can be operated as the oligomerization itself in separate batches or continuously.

The following examples 1–4 illustrate the invention without limiting its scope. Example 5 is given as a comparison and is not part of this invention.

EXAMPLE 1

Into 400 cm$^3$ of an orange-brown solution obtained by oligomerization of propylene using a catalyst obtained by reacting 1 mM of nickel octoate with 15 mM of dichloroethyl aluminum and maintained at 35° C. while agitating vigorously at atmospheric pressure (about 0.1 MPa) were bubbled successively:
(a) 120 cm$^3$ of air containing approximately 1 mM of oxygen;
(b) 1 liter of gaseous ammonia, corresponding approximately to 42 mM;
(c) then, 50 cm$^3$ of 18% by weight aqueous solution of sodium hydroxide and 50 cm$^3$ of air, while agitating vigorously.

The duration of each step is about 1 minute.

On completion of the treatment, the mixture separated into several phases. The insoluble inorganic precipitate was removed and the gaseous phase evacuated. No solid was observed at the interface of the organic and aqueous phases. The organic phase was essentially free from any inorganic element and contained less than 1 ppm by weight of each of the elements nickel, aluminum and chlorine, as was shown by analysis.

EXAMPLE 2

Under the conditions of Example 1, but with a separate treatment of the mixture in step c first with an aqueous solution of caustic soda and then with air, it was observed that after the treatment with the aqueous solution of caustic soda, the organic solution remained slightly orange-coloured, which showed the presence of nickel; but at the end of the air treatment, the organic phase was pale yellow and essentially free from any inorganic element; it contained less than 1 ppm by weight of each of the elements nickel, aluminum and chlorine, as was shown by analysis.

EXAMPLE 3

Under the same conditions as those in Example 1, but omitting the first air treatment, a small part of the nickel was found in the form of a flocculent, black solid at the imprecise aqueous-organic interface; it could not be easily removed from the solution. Analysis showed that the organic phase contained less than 1 ppm by weight of each of the elements: nickel, aluminum and chlorine.

EXAMPLE 4

Under the same conditions as in Examples 1 and 2, but omitting the final treatment with air, very little nickel was found at the aqueous-organic interface in the form of a green mixed aluminum and nickel hydroxide. The organic phase was orange, and analysis showed that it contained 3 ppm by weight of solubilized nickel.

Analysis showed that the organic phase contained less than 1 ppm by weight of each of the elements aluminum and chlorine.

EXAMPLE 5

Under the same conditions as in Example 1, but without using oxygen or a gas containing oxygen, the organic phase was slightly orange and contained, as shown by analysis, 5 ppm of nickel after a series of treatments.

What is claimed is:

1. In a method for the removal of aluminum, nickel and chlorine compounds from a liquid reaction product obtained by dimerization or codimerization of mono-olefins having two to four carbon atoms, in the presence of a catalyst obtained by the interaction of a nickel compound soluble in a hydrocarbon with an organo-aluminum chloride, comprising the steps of:
   (a) treating the liquid reaction product with anhydrous ammonia,
   (b) treating the resultant product of step (a) with an aqueous solution of alkali metal hydroxide to form an organic phase and an aqueous phase and
   (c) separating the resultant aqueous phase, and recovering a resultant organic phase containing dimerized or codimerized mono-olefins from which aluminum, nickel and chlorine have been removed,
the improvement comprising treating said liquid reaction product with oxygen or a gas containing oxygen before or during step (a), said improvement further comprising treating the product of step (a) with oxygen or a gas containing oxygen before or during step (b), all of said treating steps with oxygen or oxygen-confaining gas being conducted by bubbling said oxygen through the liquid reaction product so as to ensure substantially uniform gas-liquid contact.

2. A method according to claim 1, in which the gas containing oxygen contains 2 to 30% by volume of oxygen.

3. A method according to claim 2, in which the gas containing oxygen is air or air diluted with nitrogen.

4. A method according to claim 1, in which the oxygen/nickel molar ratio is between 0.1:1 and 10:1.

5. A method according to claim 6, in which the oxygen/nickel ratio is between 0.2:1 and 2:1.

6. A method according to claim 1, in which the anhydrous ammonia used in step (a) is used in gaseous or liquid form, in an ammonia/chlorine molar ratio of between 1:1 and 10:1.

7. A method according to claim 1, in which the aqueous solution of alkali metal hydroxide used in step (b) contains 10 to 25% by weight of sodium hydroxide.

8. A method according to claim 1, in which the volume ratio of the said organic phase to the aqueous phase is between 40:1 and 1:1.

9. A method according to claim 1, in which the treatment steps are carried out at a temperature between 20° and 80° C. and a pressure between 0.1 MPa and 5 MPa.

10. A method according to claim 1, wherein the aqueous phase separated in step (c) is recycled to step (b).

* * * * *